(12) United States Patent
Bikson et al.

(10) Patent No.: US 8,718,778 B2
(45) Date of Patent: May 6, 2014

(54) APPARATUS AND METHOD FOR NEUROCRANIAL ELECTROSTIMULATION

(75) Inventors: Marom Bikson, New York, NY (US); Abhishek Datta, New York, NY (US); Fortunato Battaglia, New York, NY (US); Maged Elwassif, Long Island City, NY (US)

(73) Assignee: Research Foundation of the City University of New York, New York, NY (US)

(*) Notice: Subject to any disclaimer, the term of this patent is extended or adjusted under 35 U.S.C. 154(b) by 325 days.

(21) Appl. No.: 12/937,950

(22) PCT Filed: Sep. 18, 2008

(86) PCT No.: PCT/US2008/010849
§ 371 (c)(1),
(2), (4) Date: Jan. 20, 2011

(87) PCT Pub. No.: WO2009/128810
PCT Pub. Date: Oct. 22, 2009

(65) Prior Publication Data
US 2011/0144716 A1    Jun. 16, 2011

Related U.S. Application Data

(60) Provisional application No. 61/124,286, filed on Apr. 15, 2008.

(51) Int. Cl.
*A61N 1/36* (2006.01)
(52) U.S. Cl.
USPC .......................................................... 607/45
(58) Field of Classification Search
USPC .................................. 607/118, 152, 45–46
See application file for complete search history.

(56) References Cited

U.S. PATENT DOCUMENTS

| | | | | |
|---|---|---|---|---|
| 4,907,601 | A * | 3/1990 | Frick | 607/72 |
| 6,748,265 | B2 * | 6/2004 | Hofmann et al. | 604/20 |
| 7,221,981 | B2 * | 5/2007 | Gliner | 607/116 |
| 2002/0188216 | A1 | 12/2002 | Kayyali et al. | |
| 2003/0018366 | A1 | 1/2003 | Lamont | |
| 2005/0004624 | A1 | 1/2005 | Gliner et al. | |
| 2006/0259094 | A1 * | 11/2006 | Naisberg et al. | 607/45 |
| 2007/0073354 | A1 * | 3/2007 | Knudson et al. | 607/45 |
| 2007/0100392 | A1 | 5/2007 | Mashino et al. | |

FOREIGN PATENT DOCUMENTS

WO    WO 2005/002664    1/2005

OTHER PUBLICATIONS

International Preliminary Report on Patentability dated Oct. 19, 2010.

\* cited by examiner

*Primary Examiner* — Amanda Patton
(74) *Attorney, Agent, or Firm* — Hoffmann & Baron, LLP

(57) ABSTRACT

There is provided method and apparatus for enhancing focality of neurocranial electrostimulation, including: providing a first plurality of electrodes having at least one electrode; providing a second plurality of electrodes having at least two electrodes; locating the first and the second plurality of electrodes on cranium of a subject and supplying electric current of opposite polarities to the first and the second plurality of electrodes. At least one electrode of the first plurality of electrodes is surrounded by at least two electrodes of the second plurality of electrodes. The enhanced focal stimulation may be used to treat ailments or augment cognitive performance. There are also provided methods for treating brain related ailments and performance augmentation.

19 Claims, 9 Drawing Sheets

_US 8,718,778 B2_

APPARATUS AND METHOD FOR NEUROCRANIAL ELECTROSTIMULATION

PRIORITY CLAIM

This is a U.S. national stage of application No. PCT/US08/10849, filed on Sep. 18, 2008. Priority is claimed on the following application(s): U.S. Application No. 61/124,286 Filed on Apr. 15, 2008, the content of which is incorporated here by reference.

TECHNICAL FIELD

The present invention generally relates to a method and an apparatus of electro-stimulation. Particularly, the present invention relates to a method of neurocranial electrostimulation.

BACKGROUND

Acute or plastic changes in brain function can be safely induced in humans by low-intensity electrical stimulation through scalp electrodes. Such electrical stimulation is known as neurocranial electrostimulation (NCS). These changes can be potentially used for therapeutic or performance enhancing applications.

Current technology generally uses stimulation through pairs of large sponge-like electrodes. Transcranial electrical stimulation conventionally refers to short-duration (50-500 μs) of supra-threshold pulses (100-1200 V). Cranial electrotherapy stimulation (CES) utilizes a range of waveforms with peak current levels ranging from 50 μA to 5 mA. Supra-threshold current pulse trains (about 0.9 A) are generally used during electroconvulsive therapy (ECT). DC waveforms normally ranging from 260 μA to 2 mA are used for transcranial direct current stimulation (tDCS). In this document, term NCS is used in a broader sense to include any stimulation using an electrode on the head or cranium.

In some cases, anodal stimulation enhances excitability, whereas cathodal stimulation reduces excitability as has been shown in several studies. Stimulation given to M1 can facilitate implicit learning and TES over the occipital cortex can facilitate visuo-motor learning. Stimulation has also been shown to alter excitability or resulting behavioral performance in somatosensory and frontopolar cortices. Cranial stimulation is being explored as a non-invasive therapeutic option for the treatment of neurological and psychiatric disorders including depression, stroke, Alzheimer's, and learning disorders. A critical limitation for cranial stimulation efficacy and safety is derived from the need for accurate control of exactly where in the brain the stimulation actually modulates the neuronal activity. TES, and analogous Transcranial Direct Current Stimulation ("tDCS"), are considered to be poorly focused using common "remote bipolar" electrode configuration.

It is therefore an object of the present invention to provide a stimulation system which can accurately target brain modulation.

It is another object of the present invention to provide a stimulation system whose design and application benefits from insights derived from biophysical studies in order to better functionally target specific areas of the brain for more accurate electrostimulation.

It is a further object of the present invention to provide a system which enables more effective and safer cranial stimulation with accurate control of what part of the brain is stimulated for modulating neuronal activity.

SUMMARY

The present invention provides method and apparatus for neurocranial electrostimulation using electrodes, as further described below. In preferred embodiments of the invention, such electrodes are located on the head or areas associated with the head of the subject, including the cranium, scalp, face, neck, ears, eyes, forehead, cheek, chin, nose, and mouth. The following description shall be understood to apply to various of these embodiments, and therefore to various areas of the head. It will be appreciated that the invention is not limited by any illustrative embodiment described only with respect to one particular area of the head, such as the cranium.

According to a first aspect, there is provided a method for neurocranial electrostimulation. The method includes—providing a first plurality of electrodes having at least one electrode; providing a second plurality of electrodes having at least two electrodes; locating the first and the second plurality of electrodes on cranium of a subject and supplying electric current of opposite polarities to the first and the second plurality of electrodes. Upon locating on cranium of a subject, at least one electrode of the first plurality of electrodes is surrounded by at least two electrodes of the second plurality of electrodes.

According to a second aspect, there is provided another method for neurocranial electrostimulation. The method includes—providing a first plurality of electrodes having at least one electrode; providing a second plurality of electrodes having at least one annular electrode having an opening; locating the first and the second plurality of electrodes on cranium of a subject; and supplying electric current of opposite polarities to the first and the second plurality of electrodes. Upon locating on cranium of the subject, at least one electrode of the first plurality of electrodes is located within the opening of at least one annular electrode of the second plurality of electrodes.

According to a third aspect, there is provided an apparatus for neurocranial electrostimulation. The apparatus includes: a first plurality of electrodes having at least one electrode; a second plurality of electrodes having at least three electrodes; fixing means for locating the first and the second plurality of electrodes on cranium of a subject; and a source of electric current. The source of electric current provides electric current of opposite polarities to the first and the second plurality of electrodes. In one embodiment, the first plurality is provided with positive polarity current while the second plurality is provided with negative polarity current.

According to a fourth aspect, there is provided a method of treating a human being suffering from a brain related ailment. The method includes: providing a first plurality of electrodes; providing a second plurality of electrodes; locating the first and the second plurality of electrodes on cranium of a subject; and supplying electric current of opposite polarities to the first and the second electrodes. Up on locating on cranium of subject, at least one electrode of the first plurality of electrodes is surrounded by at least two electrodes of the second plurality of electrodes. The number of electrodes and the location of the electrodes may be suitably selected depending up on the ailment.

According to a fifth aspect, there is provided a method of affecting human cognitive performance. The method includes: providing a first plurality of electrodes; providing a second plurality of electrodes; locating the first and the second plurality of electrodes on cranium of a subject; and supplying electric current of opposite polarities to the first and the second electrodes, wherein at least one electrode of the first plurality of electrodes is surrounded by at least two electrodes of the second plurality of electrodes.

According to a sixth aspect, there is provided a method of modulating brain function, the method includes: providing a first plurality of electrodes; providing a second plurality of electrodes; locating the first and the second plurality of electrodes on cranium of a subject; and supplying electric current of opposite polarities to the first and the second electrodes, wherein at least one electrode of the first plurality of electrodes is surrounded by at least two electrodes of the second plurality of electrodes.

Definitions

The following words and terms used herein shall have the meaning indicated:

Unless specified otherwise, the terms "comprising", "including", "having", "comprise" and grammatical variants thereof, are intended to represent "open" or "inclusive" language such that they include recited elements but also permit inclusion of additional, un-recited elements.

"Focality" indicates the spatial extent of the intensity of electric field in the head and/or brain. Focality can be determined by how small the region in the brain that a significant electric field or current density is induced in by stimulation.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value. Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

DETAILED DISCLOSURE OF EMBODIMENTS

Figure 1A:
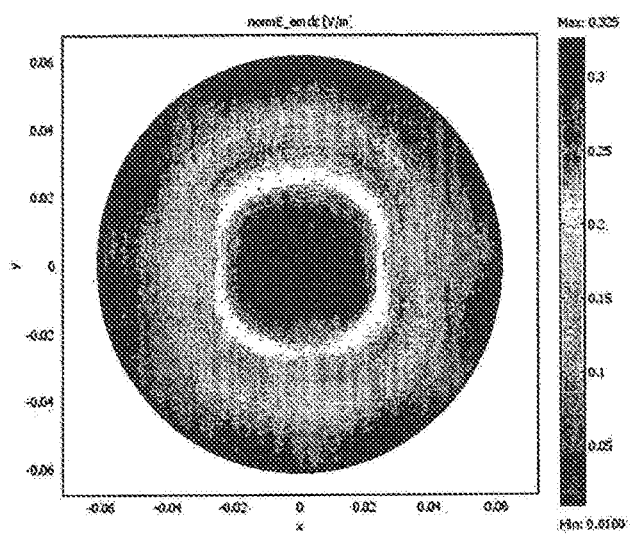
FIG. 1A is a diagrammatic surface plot of the peak magnitude electric field (V/m) for a "remote bipolar" configuration.

There is provided a first plurality of electrodes and a second plurality of electrodes. The electrode may be any suitable electrical appliance capable of carrying current. Neurocranial stimulation is the use of electrical current to change neuronal function in the head with at least one electrode positioned on the surface of the head. Neurocranial stimulation includes stimulation of the brain, the eyes, the cranial nerves, peripheral nerves in the head, sensory nerves in the head, motor nerves in the head, stimulation of structures deep in the head, stimulation of the cortex, stimulation of cortical regions, stimulation of the cerebellum, stimulation of axons of passage in the head, stimulation of the hippocampus, stimulation of the thalamus, stimulation of a combination of the above structures, and stimulation of nervous system structures that directly or indirectly connect to the above listed structures. Neurocranial stimulation is distinct from applications where the primary aim is to stimulate muscle, stimulate skin, assist with drug delivery from the electrodes themselves, or measure resistance, however neurocranial stimulation may be used in conjunction with these separate approaches.

Electrodes

Various types of electrodes may be suitable for cranial stimulation and several embodiments of electrodes in practice of the invention are disclosed below. The electrodes of first and second plurality of electrodes may be made of any suitable material or combination of materials capable of carrying current. In addition, the electrodes may have non-conductive components. In a particular embodiment, the electrodes are made of materials selected from the partial group consisting of copper, aluminum, magnesium, steel, iron, carbon, graphite, silver, sponge, pad, silver chloride, sintered silver chloride, rubber, conductive rubber, gold, tungsten, titanium, ceramic, platinum, platinum-iridium, metal alloy, conductive gel, conductive fluid, polymer, conductive polymer. In an embodiment according to the invention, different electrodes in the plurality of electrodes are made of different materials; for example, the first plurality of electrodes may include 2 copper electrodes and 2 silver electrodes. In yet another embodiment, the electrodes are Ag/AgCl electrodes made by A-M Systems, WA, USA The electrodes may have any suitable size. Unless otherwise stated, the shape of the electrode refers to the shape of the portion of the electrode in contact with the subject. More specifically, in preferred embodiments of the invention, the electrodes are located on the head or areas associated with the head of the subject, including the scalp, face, neck, ears, eyes, forehead, cheek, chin, nose, and mouth. The following description may be understood to apply to various of these embodiment, and therefore to various areas of the head, even while an illustrative embodiment may be described only with respect to one particular area of the head. In one embodiment, the electrodes are circular in shape. In another embodiment, the electrodes have a shape suitably selected from the group consisting of triangle, rectangle, quadrilateral, circular and polygonal. In yet another embodiment the electrodes is an annular electrode with an opening. The opening of the annular electrode may be of any shape suitably selected from the group consisting of circle, triangle, quadrilateral, square, pentagon, hexagon, heptagon, octagon and ellipse. In a particular embodiment the opening is circular in shape.

Different electrodes in the plurality of electrodes may have different shapes. Different electrodes in the plurality of electrodes may be made of different combinations of materials. In a preferred embodiment, the electrodes are circular silver disks 8 mm in diameter and having 2 mm radial width. The electrode may be commercially available electrodes fabricated for biological or non-biological applications, including EEG applications and brain stimulation applications.

Electrode Fixing Means

In a method according to the invention, the electrodes are located on the cranium of a subject. Cranium is used here to refer to the whole head including the face, neck, ears, eyes, fore-head, cheek, chin, nose, and mouth. In one embodiment the electrodes are positioned on the skin or scalp over the cranium. In another embodiment some electrodes are positioned over the cranium and other electrodes are positioned elsewhere on the head. In yet another embodiment, all of the electrodes are positioned on the head in locations not directly on the cranium. In yet another embodiment some electrodes are positioned on the neck. In yet another embodiment some electrodes are positioned on the neck. The method according to the invention may be used to stimulate any part of nervous system including but not limited to spinal cord, cerebellum, brain stem, temporal lobe, occipital lobe, parietal lobe, frontal lobe and other parts of brain and nervous system.

In one embodiment, the cranial electrode positioning cap is made out of suitable material (i.e. material that is comfortable and formable and adequately robust for electrode attachment) and is designed to allow positioning of the stimulating electrodes on the head. In another embodiment the cranial electrode positioning cap is a hood which is circular in shape. In another embodiment, the cranial electrode positioning cap is a flexible material that can take the shape of a head and it fitter with a strap. In yet another embodiment, the electrode positioning cap is made from mesh. In yet another embodiment, the electrode positioning cap is in strip form. In yet another embodiment, the electrode positioning cap is a band form. In yet another embodiment, the electrode positioning cap is a combination of stings of wires. In yet another embodiment, the electrode positioning cap includes a helmet. In yet another embodiment, the electrode positioning cap has receptors for positioning one or more stimulating electrodes. In yet another embodiment, the stimulation electrodes are fixed in the cranial electrode positioning cap. In yet another embodiment the electrodes may be attached to the cranial electrode position cap. In yet another embodiment, the electrode positioning cap is customized to individuals. In yet another embodiment, the electrode positioning cap is fitted with sensors. In yet another embodiment, the electrode positioning cap is fitted with metal components. In yet another embodiment, the electrode positioning cap is fitted with plastic components In yet another embodiment, the electrode positioning cap is positioned around the neck. In yet another embodiment, the electrode positioning cap is held in place by an external manipulation of fixing system. In yet another embodiment, the electrode positioning cap is a made of MRI safe material. In yet another embodiment, the electrode positioning cap is made of one or more clips.

Source of Electric Current

Each electrode is connected to a source of electrical current. Term Source is used here to mean a source of electric current that can provide electric current of both polarities. Electrodes of a given plurality may be connected to the same electrical current source or they may be connected to separate current sources. Electrodes of first and second plurality are provided with electric current of opposite polarities. In one embodiment, the first plurality of electrodes is provided with electric current of positive polarity while the second plurality electrodes are provided with electric current of negative polarity. In another embodiment, the first plurality electrodes are provided with negative polarity current and the second plurality are provided with positive polarity current. The magnitude of current provided to the first and the second pluralities may be equal. As the first and the second pluralities are provided with electric current of opposite polarities, it may be viewed as supply and withdrawal of electric current. Accordingly, one may imagine that the first plurality of electrodes is pushing current into the cranium while the second plurality is withdrawing current from the cranium. In another embodiment, the second plurality may supply the current and the first plurality may withdraw the current.

The electric current may be provided by any suitable source of electric current. The source of current may be current controlled, or voltage controlled, or charge controlled, or capacitive, or triggered, or adaptive, or programmable, or high-resistance, or low resistance, or feed-back controlled or a combination, or a variation of these. In one embodiment, the magnitude of electric current provided to the electrodes is selected from the group consisting of 0.001 to 100 mA, 0.1 to 100 mA, 1 mA to 100 mA, 2 mA to 50 mA. In a particular embodiment electric current of mA is provided to the electrodes. In another embodiment a current of 2 mA is provided. In yet another embodiment 3 mA is provided to the electrodes. In another embodiment the electric voltage applied across the electrodes is selected from the group consisting of 0.001 V to 1 V, 0.001 V to 10 V, 0.1 V to 100 V, 1 V to 100 V and 1 V to 1000 V. The current may be fixed over time or the current may change over time. For each electrode and for a combination of electrodes the total current or the total voltage or both may be limited. The current may change similarly for each electrode, or may change independently at each electrode. The current may be zero during a portion of time. The current at one electrode may vary depending on the current at the other electrode. For example the current at one electrode may be a fraction of the current at another electrode or a multiple of a current at another electrode. The current at one electrode may similarly depend on the current at a combination of other electrodes. For example the current at one electrode may be the sum of current at other electrodes. The source of current may be monophasic, biphasic, charge balanced, charge imbalanced, AC, DC, sinusoidal, triangular, square, pulsed, pulse train, low-frequency, high-frequency, amplitude modulated, or a combination of these. The current may be ramped up at the start of stimulation and ramped down at the end of stimulation. The current may be controlled by the subject or by the device operator or by both.

A first electric current provided to the first plurality of electrodes may be divided before it reaches an individual electrode in the first plurality of electrodes. For example, a total current of I1 provided by the first electric source may be divided into I2, I3 and I4. Three different electrodes in the first plurality may be provided with currents I2, I3 and I4 respectively. The division of current may be an equal division or it may be any other suitable division. The total amount of current of one plurality or the division of current between electrodes of a single plurality may vary over time. The total amount of current of one plurality or the division of current between electrodes of a single plurality may vary depending on a user defined variable. The total amount of current of one plurality or the division of current between electrodes of a single plurality may vary depending on the condition of the electrodes, positioning of the electrodes, condition of the subject, or desired stimulation outcome. For example, the current divided into three electrodes I7, I8, and I9 may vary depending the resistance of each electrode.

The total current provided to the first plurality and the second plurality of electrodes is equal in magnitude. The concept may be explained by analogy to water current. Just like water could be pumped into a tank and pumped out of the tank, electric current may be pushed into and pulled out of cranium. In the method according to the invention, the total current pushed into cranium of a subject and total current pulled out of the cranium are equal. Either of the first and the second current could be viewed as the current being pushed in.

Surrounding of Electrodes

The electrodes used for neurocranial stimulation may be arranged in many suitable configurations. In one embodiment, the electrodes are arranged in a manner that at least one electrode of the first plurality of electrodes is surrounded by at least two electrodes of the second plurality of electrodes. The concept of surrounding basically excludes any co-linear configurations of electrodes where two electrodes of second plurality are located on same side of one electrode of the first plurality of electrodes. According to the invention, two electrodes, say A & B, surround a third electrode, C, if they are located on opposite sides of the third electrode. In other words, electrodes A and B are located on opposite sides of electrode C.

Triangular Configuration

Figure 8:
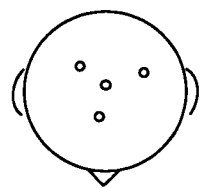
FIG. 8 illustrates a triangular configuration of electrodes.

Surrounding of electrodes may be achieved by various configurations. In one embodiment, the electrodes are arranged in a triangular configuration. In a triangular configuration, the first plurality of electrodes includes at least one electrode while the second plurality of electrodes includes at least three electrodes. The three electrodes of the second plurality form three vertices of an imaginary triangle while one electrode from the first plurality is located inside the imaginary triangle. FIG. 8 illustrates a triangular configuration of electrodes.

Concentric Ring Configuration

Figure 9:
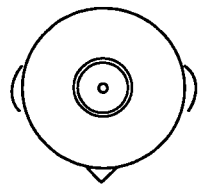
FIG. 9 illustrates a concentric ring configuration of electrodes.

In another embodiment, the electrodes may be arranged in a concentric ring configuration. In this embodiment, the first plurality includes one electrode and the second plurality comprises of one ring shape electrode. The one electrode of first plurality is located inside the perimeter of the ring shape electrode of the second plurality of electrodes. FIG. 9 illustrates a concentric ring configuration of electrodes. The electrode comprising the first plurality may itself be a ring shaped electrode.

Double Concentric Ring Configuration

Figure 10:
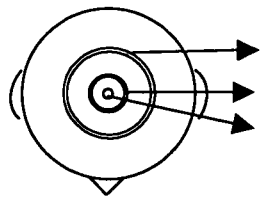
FIG. 10 illustrates a concentric ring configuration of electrodes.

In yet another embodiment, the electrodes may be arranged in a double-concentric ring configuration. In this embodiment, the first plurality includes one electrode and the second plurality includes two ring shape electrodes. The one electrode of first plurality is located inside the perimeter of at least one ring shape electrode of the second plurality of electrodes. FIG. 10 illustrates a concentric ring configuration of electrodes.

4×1 Ring Configuration

Figure 11:
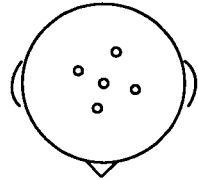
FIG. 11 illustrates a 4×1 ring configuration of electrodes.

In further embodiment, the electrodes may be arranged in a 4×1 ring configuration. In this embodiment, the first plurality includes one electrode while the second plurality includes four electrodes. The one electrode of first plurality is located inside an imaginary quadrilateral formed by the four first plurality electrodes. FIG. 11 illustrates a 4×1 ring configuration of electrodes.

3×3 Configuration

In another embodiment, the electrodes may be arranged in a 3×3 configuration. In this embodiment, the first plurality includes three electrodes while the second plurality also includes three electrodes. There are multiple ways to form a 3×3 configuration. In one embodiment, one electrode of the first plurality is located inside an imaginary triangle formed by the three second plurality electrodes. In another embodiment, the three electrodes of each of the first and the second plurality are arranged in collinear manner. The linearly arranged electrodes may be placed in parallel stripes. The linearly arranged electrodes may be placed in intersecting stripes. The 3×3 electrodes may form two imaginary triangles wherein one triangle is enclosed in the second triangle. In another embodiment, the two imaginary triangles partially overlap.

The spatial location of the 3×3 electrodes is suitably selected depending on the area of cranium to be stimulated.

4×4 Configurations

In another embodiment, the electrodes may be arranged in a 4×4 configuration. In this embodiment, the first plurality comprises of four electrodes while the second plurality also comprises of four electrodes. There are multiple ways to form a 4×4 configuration. In one embodiment, one electrode of the first plurality is located inside an imaginary quadrilateral formed by the four second plurality electrodes. In another embodiment, the four electrodes of each of the first and the second plurality are arranged in collinear manner. The linearly arranged electrodes may be placed in parallel stripes. The linearly arranged electrodes may be placed in intersecting stripes. The 4×4 electrodes may form two imaginary quadrilaterals wherein one quadrilateral is enclosed in the second quadrilateral. In another embodiment, the two imaginary quadrilaterals partially overlap. The spatial location of the 4×4 electrodes is suitably selected depending on the area of cranium to be stimulated.

Polygonal Configuration

Figure 12:
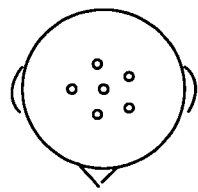
FIG. 12 illustrates a pentagonal (polygonal) configuration of electrodes.

In another embodiment, the electrodes may be arranged in a polygonal configuration. In this embodiment, the first plurality comprises of one electrode while the second plurality comprises of five or more electrodes. The one electrode of first plurality is located inside an imaginary polygon formed by the second plurality electrodes. FIG. 12 illustrates a pentagonal (polygonal) configuration of electrodes.

Methods of Treatment

There is provided a method for neurocranial electrostimulation comprising: providing a first plurality of electrodes comprising at least one electrode; providing a second plurality of electrodes comprising at least one annular electrode having an opening; locating the first and the second plurality of electrodes on cranium of a subject; and supplying electric current of opposite polarities to the first and the second plurality of electrodes, wherein at least one electrode of the first plurality of electrodes is located within the opening of at least one annular electrode of the second plurality of electrodes.

The method of neurocranial electrostimulation according to the invention may be used to treat a mammal suffering from a nervous system related ailment. Accordingly, there is provided a method of treating a human being suffering from a brain related ailment, the method comprising: providing a first plurality of electrodes; providing a second plurality of electrodes; locating the first and the second plurality of electrodes on cranium of a subject; and supplying electric current of opposite polarities to the first and the second plurality of electrodes, wherein at least one electrode of the first plurality of electrodes is surrounded by at least two electrodes of the second plurality of electrodes.

The method of treatment according to the invention may be used to treat an ailment selected from the group consisting of depression, movement disorder, Parkinson's disease, epilepsy, memory loss, stroke, obsessive compulsive disorder, sleep disorder, mood disorder, schizophrenia, manic disorder, attention deficit disorder, attention deficit hyper-activity, disorder, pain, chronic pain, tumor, carpal tunnel syndrome, coma, persistent vegetative state, Creutzfeldt-Jakob disease, narcolepsy, dyslexia, head injury, migraine, prion diseases, dementia, and neurological manifestations of AIDS. In another embodiment, the method of neurocranial stimulation is used to enhance cognitive performance of a human being. The cognitive performance task may be selected from the group consisting of a memory task, a speaking task, a fluency task, a sleep task, sleep/wake task, a recognition task, a selection task, a motor task, an attention task, a reasoning task, a focus task and an understanding task, reaction time, general intelligence, a perception task, and decision tasks.

Combination with Drugs

The method of neurocranial stimulation may be applied in conjunction with a drug. In such a method, a subject is administered with a drug and then subject to electrostimulation. In an embodiment the stimulation is applied in conjunction with a drug or pharmaceutical agent. The drug may be administered before, during, or after stimulation or following a specific temporal relationship relative to stimulation. The drug may cancel, buffer, augment, modulate, or alter the effects of stimulation. The stimulation may cancel, buffer, modulate, or alter the effects of the drugs. The stimulation may be used to regulate the rate or degree of drug action over time. The drug may be administered through multiple means including, but not limited to, orally, systemically, through a pump, or transdermaly.

EXAMPLE

Neurocranial Electrostimulation (NCS) method according to the invention is demonstrated below. The TES method of the present invention enhances focality of the electric current inside cranium of a subject.

In this work, Neurocranial Electrostimulation induced electric fields are calculated using a four layer concentric spheres model of the human head. These layers represent the scalp, the skull, the cerebrospinal fluid, and the brain.

As the induced electric field must have a component that is parallel to the neuronal structure in order to stimulate the neuron and as cortical neurons extend roughly perpendicular to the surface, the electric field normal to the brain surface is a useful indicator of effectiveness of neurocranial stimulation. The electric field normal to the brain surface was determined in this work. Further, the second derivative of the electric field is an indicator of activation. We compared the effects of TES stimulation with remote scalp electrodes ("remote bipolar" configuration), adjacent scalp electrodes ("bipolar" configuration), "belt" electrodes, "tripolar" configuration and "concentric ring" configuration and several additional configurations. The knowledge of the electric field distributions inside the brain for different electrode placements provides useful information for development of clinical protocols to treat brain related ailments.

The head model was treated as a 3-D inhomogeneous medium containing concentric spheres; each sphere was homogeneous and isotropic. The four layer concentric model is widely used and accepted for its quantitative agreement with a variety of general observations of the electroencephalogram. Four concentric zones each with uniform conductivities of 61.53 mm, 64.03 mm, 71.76 mm, and 76.49 mm radii represent the brain tissue, the cerebrospinal fluid, the skull, and the scalp respectively. The electrical properties of the four layers of the model were taken from standard sources 17. The dimensions of the head are based on a 26 year old male 16.

The electrode configurations modeled were:

"Remote bipolar": Simulation with two electrodes (active and reference). The active electrode was placed over CZ in accordance with the 10-20 EEG system and the reference electrode at the forehead above the contralateral orbita to model the transcranial stimulation of the primary motor cortex.

"Bipolar": Simulation with the active electrode placed over C3 and the reference electrode over CZ. C3 and CZ refers to electrode positions on cranium of a subject. The position names are in accordance with standard naming convention accepted in the technical field.

"Belt": Simulation with the reference electrode consisting of a belt (2 mm) wide, circling the forehead with the active electrode placed on C3.

"Tripolar": Simulation with two active electrodes: first electrode over C3, and second electrode over CZ, and the reference electrode placed over the forehead above the contralateral orbita.

"Concentric Ring": Simulation with (an active electrode of outer diameter: 11 mm and inner diameter: 9 mm enclosing the reference electrode) over C3.

Unless indicated otherwise, all the electrodes used in the model were circular disks 8 mm in diameter as have been used clinically 4, and having radial width 2 mm. The electrodes were modeled as conductors with the conductivity of copper ($5.8 \times 10^7$ S/m).

The following laplace equation was solved:

$$\nabla \cdot (\sigma \nabla V) = 0$$

where V is potential; σ is conductivity, with boundary conditions—
1) Active inward current flow=$J_n$, (normal current density) applied to the distal surface of the active electrode(s),
2) ground applied to the distal surface of the reference electrode,
3) all other external surfaces treated as insulated The injected current had 1 mA amplitude to model the "remote bipolar" stimulation and for all other configurations the injected current density was adjusted to obtain surface plots of normal electric field of similar peak magnitudes.

FEMLAB 3.2 (from COMSOL Inc., Burlington, Mass.) was used to solve the finite element models. The model was meshed into more than 170,000 quadratic elements and more than 27000 boundary elements for each of the simulations. This provided a compromise between accuracy of the solution and processing time. "Surface plots" were generated by plotting the normal electric field (to the surface) on the top half of the innermost sphere in the model (i.e. brain). "Cross-section plots" were generated by plotting the normal electric field, sliced through the sphere centers including the center of the active electrode. In the case of "tripolar" stimulation (where there was no radial symmetry), the cross-section plots included the centers of one of the two active electrodes and the reference electrode.

In separate studies, the electrode was not altered, but a conductive material was added, contacting the electrode, with the above geometries. In separate studies, insulating or grounding material was used around either the electrode of conductive materials. In separate studies, the current distribution to each electrode was altered. In separate studies, electrodes were grounded or connected together.

Figure 1B:
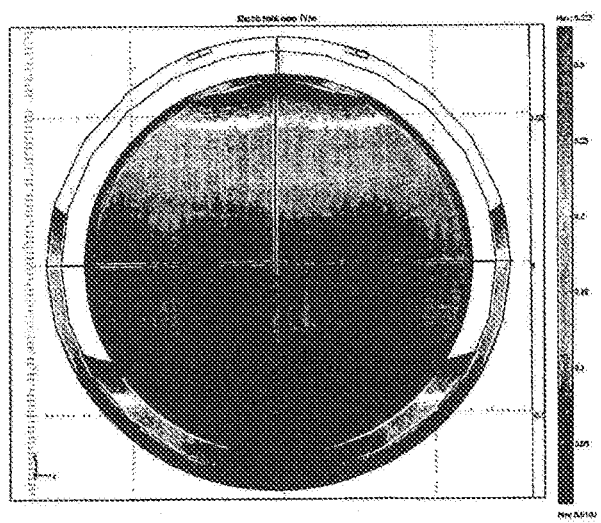
FIG. 1B is a diagrammatic cross-section plot of the peak magnitude electric field V/m) for a "remote bipolar" configuration.
Figure 2A:
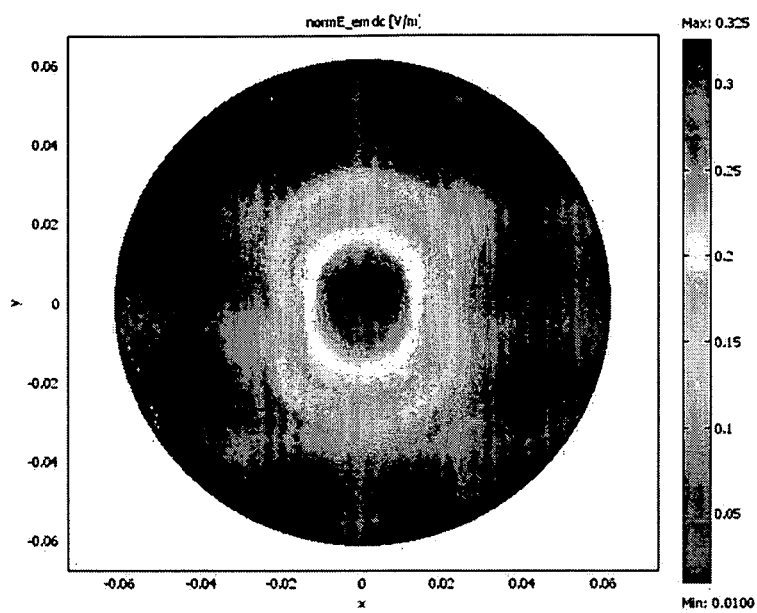
FIG. 2A is a diagrammatic surface plot of the peak magnitude electric field (V/m) for a "bipolar" configuration.
Figure 2B:
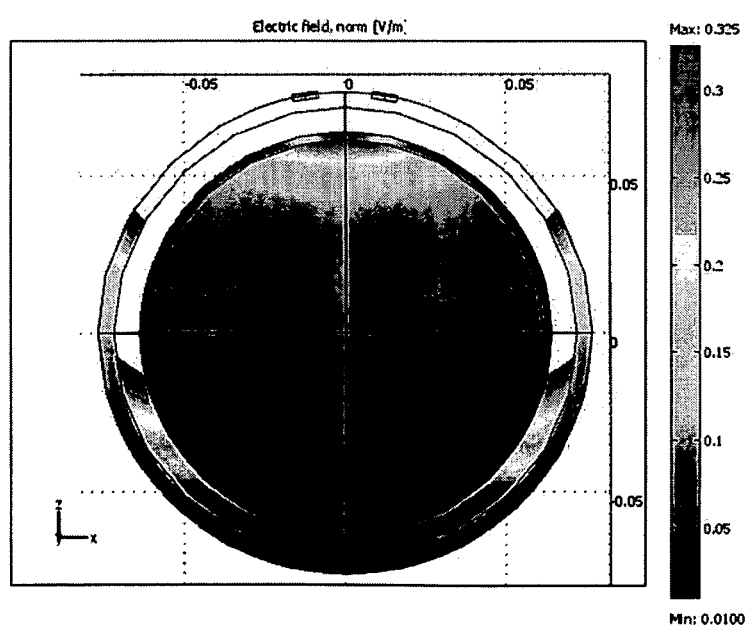
FIG. 2B is a diagrammatic cross-section plot of the peak magnitude electric field (V/m) for a "bipolar" configuration.

For all configurations the low conductivity of the skull relative to the scalp, shunts most of the current through the scalp, consistent with previous neurocranial stimulation studies 1.28 mA, 1.3 mA, 0.8 mA (for each active electrode), 8.04 mA was required by "bipolar", "belt", "tripolar", "concentric ring" configurations respectively to induce normal surface electric field of comparable peak magnitude as those induced by 1 mA "remote bipolar" NCS stimulation. "Remote bipolar" results in diffuse activity under and between the active electrode and the reference electrode. See FIG. 1A which is a diagrammatic surface plot of the peak magnitude electric field (V/m) for "remote bipolar" configuration. Close "bipolar" stimulation is more focal than "remote bipolar" but higher current stimulation intensities are needed to produce the same peak electric field response. See FIG. 2A which is a diagrammatic surface plot of the peak magnitude electric field (V/m) for a bipolar configuration. Consistent with previous studies, we found that with "remote bipolar" stimulation, the current density decreases much less rapidly with depth and stimulates a wider region than does "bipolar" stimulation. See FIG. 1B and FIG. 2B which are, respectively, a diagrammatic cross-section plot of the peak magnitude electric field (V/m) for a remote bipolar configuration and a diagrammatic cross sectional plot of the peak magnitude electric field (V/m) for a "bipolar" configuration.

Figure 3A:
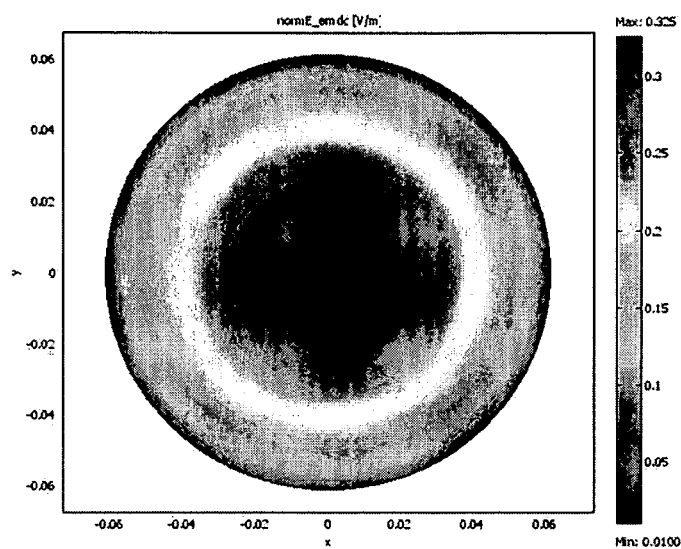
FIG. 3A is a diagrammatic surface plot of the peak magnitude electric field (V/m) for a "belt" configuration.
Figure 3B:
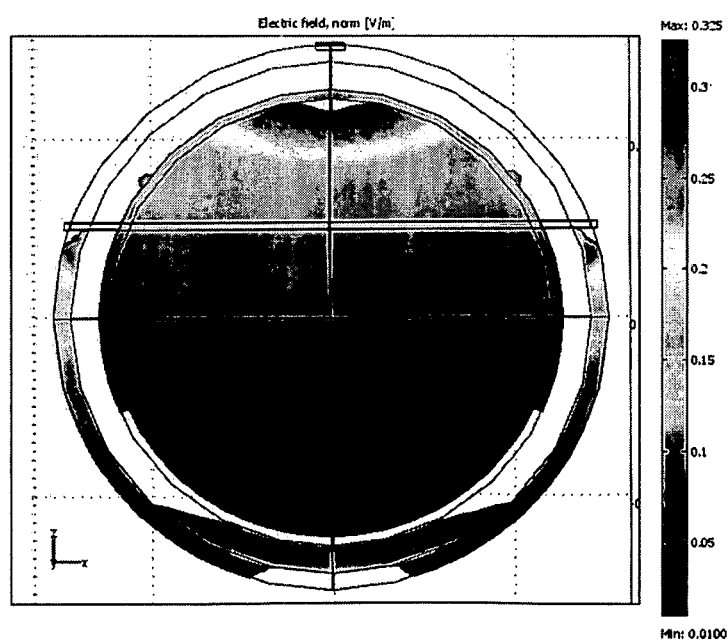
FIG. 3B is a diagrammatic cross-section plot of the peak magnitude electric field (V/m) for a "belt" configuration.

"Belt" stimulation is not only less focal than "remote bipolar" stimulation, but requires more total current (FIG. 3A). As expected the electric field lines are radially distributed on the surface as they flow from the active electrode to the surface circumscribed by the reference electrode.

Figure 4A:
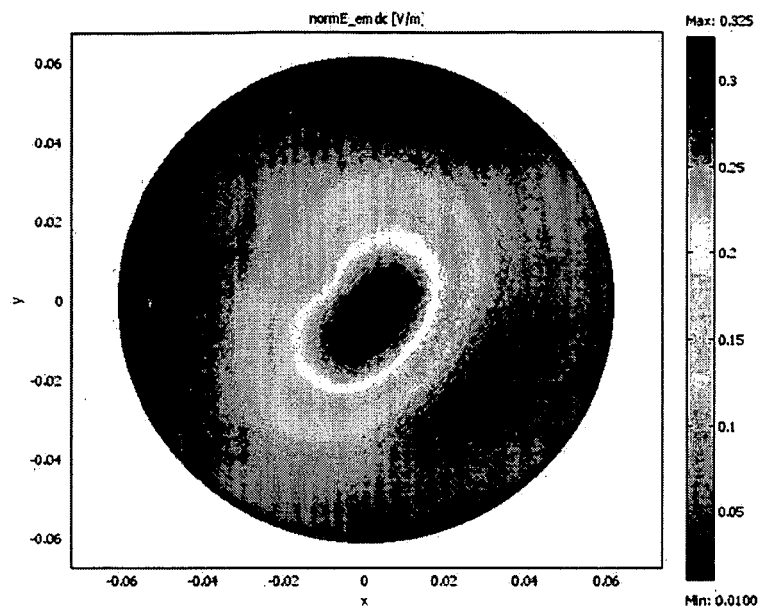
FIG. 4A is a diagrammatic surface plot of the peak magnitude electric field (V/m) for a "tripolar" configuration.
Figure 4B:
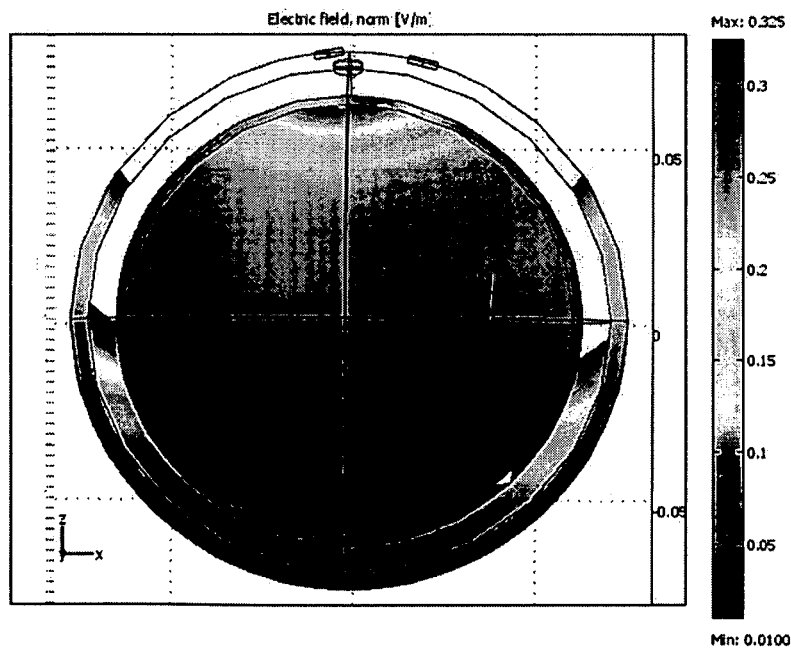
FIG. 4B is a diagrammatic cross-section plot of the peak magnitude electric field (V/m) for a "tripolar" configuration.

"Tripolar" stimulation was found to have similar region of influence (FIG. 4B) as "bipolar" stimulation, but needed more total current, but less current density (since current was divided across two active electrodes).

Figure 5A:
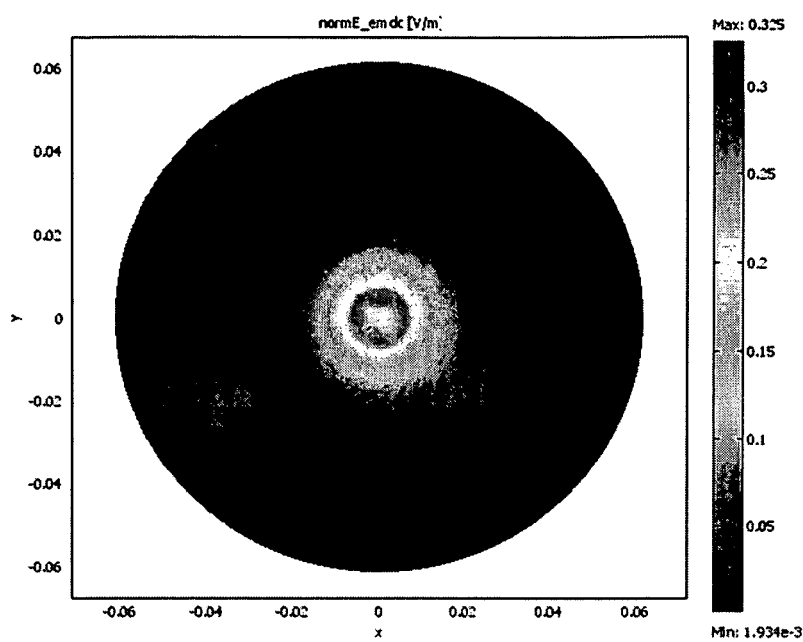
FIG. 5A is a diagrammatic surface plot of the peak magnitude electric field (V/m) for a "ring" configuration.
Figure 5B:
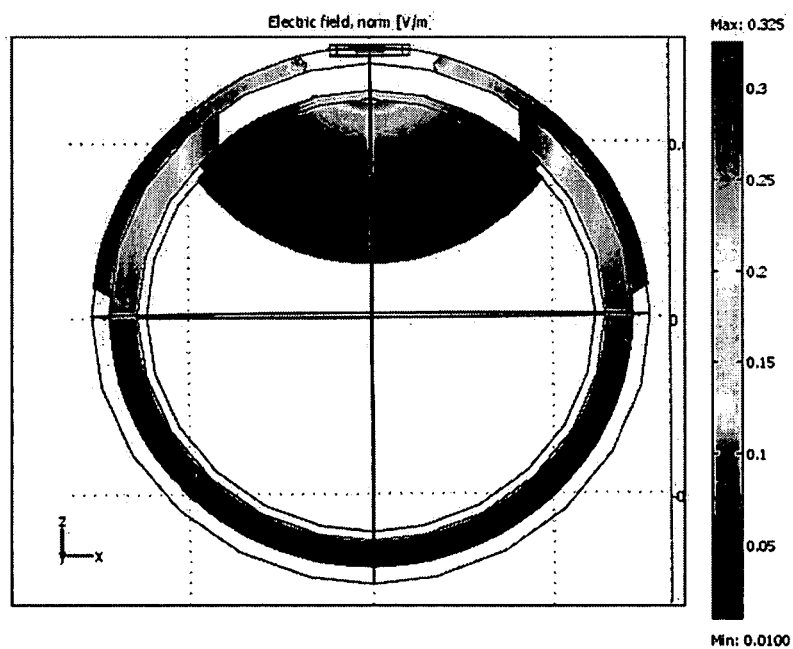
FIG. 5B is a diagrammatic cross-section plot of the peak magnitude electric field (V/m) for a "ring" configuration.

The "concentric ring" led to the greatest increase in focality (FIG. 5A) at the expense of increased injected current. The current density decreased much more rapidly with depth in comparison to all the other stimulation scenarios (FIG. 58).

Figure 6A:
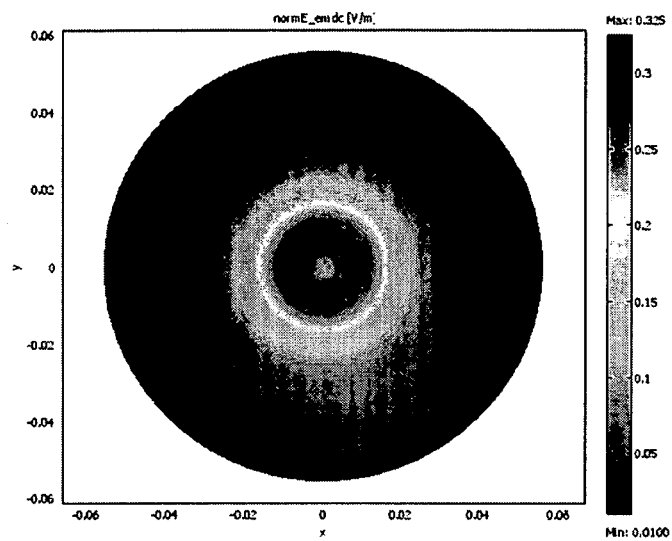
FIG. 6A is a diagrammatic surface plot of the peak magnitude electric field (V/m) for a "double concentric ring" configuration.
Figure 6B:
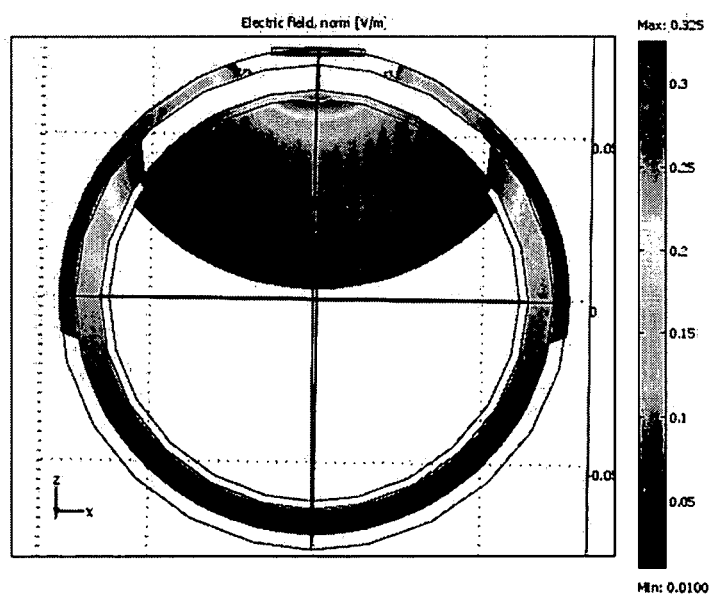
FIG. 6B is a diagrammatic cross sectional plot of the peak magnitude electric field (V/m) for a "double concentric ring" configuration.
Figure 7A:
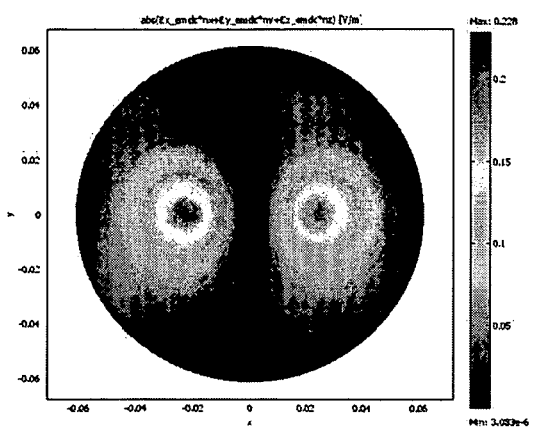
FIG. 7A is a diagrammatic surface normal plot of the electric field (V/m) for a "remote bipolar" configuration.
Figure 7B:
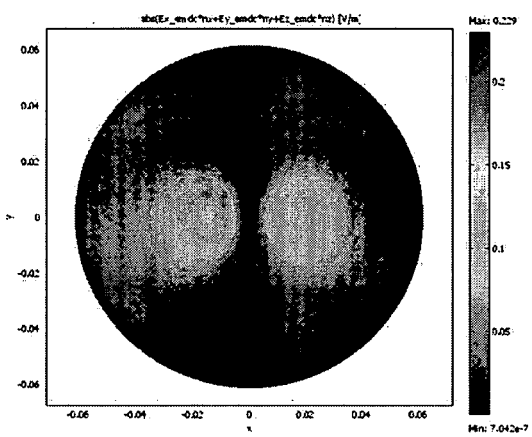
FIG. 7B is a diagrammatic surface normal plot of the electric field (V/m) for a "bipolar" configuration.
Figure 7C:
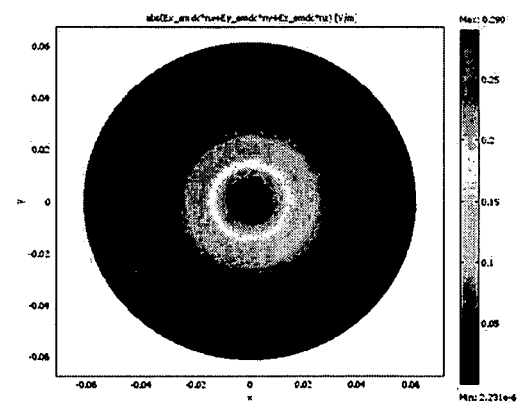
FIG. 7C is a diagrammatic surface normal plot of the electric field (V/m) for a "belt" configuration.
Figure 7D:
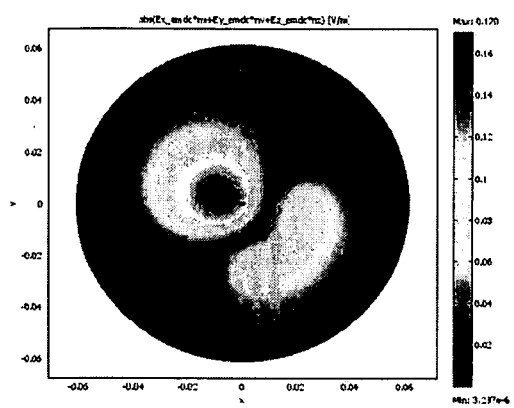
FIG. 7D is a diagrammatic surface normal plot of the electric field (V/m) for a "tripolar" configuration.
Figure 7E:
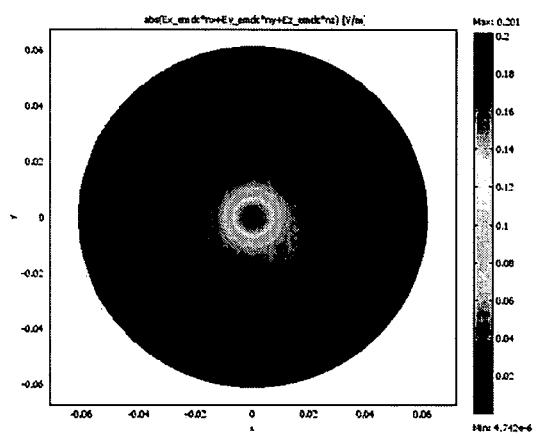
FIG. 7E is a diagrammatic surface normal plot of the electric field (V/m) for a "ring" configuration.
Figure 7F:
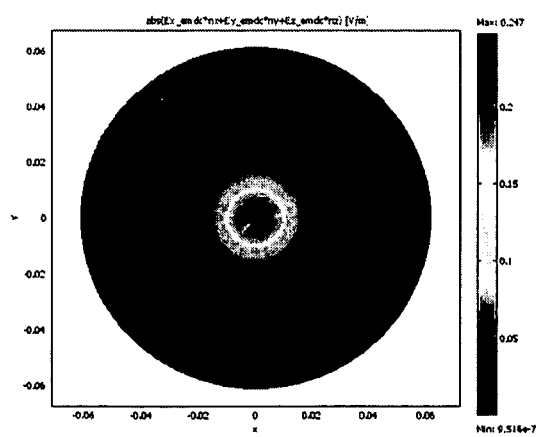
FIG. 7F is a diagrammatic surface normal plot of the electric field (V/m) for a "double concentric ring" configuration.

Although the "double concentric ring" required the maximum current of all, it may be suited to target circular structures around the head apex. See FIG. 6A, which is a diagrammatic surface plot of the peak magnitude electric field (V/m) for a "double concentric ring" configuration. The "surface" plots and the "surface normal" plots of both the "ring" and "double concentric ring" configurations are similar. See FIGS. 5A and 7E, which are, respectively, again a diagrammatic surface plot of the peak magnitude electric field (V/m) for a "ring" configuration, and a diagrammatic surface normal plot of the electric field (V/m) for a "ring" configuration. See FIGS. 6A and 7F, which are, respectively, a diagrammatic surface plot of the peak magnitude electric field (V/m) for a "double concentric ring" configuration, and a diagrammatic surface normal plot of the electric field (V/m) for a "double concentric ring" configuration. "Surface" plots and "surface normal" plots are one example allowing targeting of specific anatomical and functional structures. Double concentric ring is, in addition to a novel geometry, an application of a combination of multiple electrodes and designs.

Since the static field approximation in our model implies conservation and linearity of the electric field solution, different surface normal electric field values can be extrapolated for any current magnitude from our results by simple scaling. Similarly, if current magnitudes change over time (temporal waveform) the model can be used to determine the current/voltage distribution at any given time.

We further investigated positioning the electrodes in various locations and distance along the cranium, where cranium indicates any location on the head. Electrodes were position in locations corresponding to the face, the neck, the ears, the eyes, the scalp, and the nose. It was found that by selection the electrode position, the targeting and the focality of stimulation could be controlled.

Electrode geometries can be used to control stimulation focality. The number of electrodes used can be used to control stimulation focality. The current destitution to electrodes used can control stimulation focality. The use of conductive or insulation material can control stimulation focality. The combination of these can define a stimulation configuration. FEM solvers can be used to predict focality.

A region of the brain of interest may be stimulated using the appropriate stimulation configuration involving electrode geometry, number of electrodes, current distribution, and material properties used.

Multiple regions of the brain may be stimulated in sequence or concurrently through combination of appropriate stimulation configuration involving electrode geometry, number of electrodes, current distribution, and material properties used.

Any temporal waveforms to any combination of electrodes may be used with any given configuration including changing current distribution to each electrode over time or setting current to one or more electrodes to zero.

In separate studies, the geometry suggested above may be used in combination and multiple electrodes with any combination of geometries. The focality may be estimated by combination of the previous results and through novel analysis using similar techniques.

The geometry and the current distribution of the electrodes were altered to target structure superficial in the head. The geometry and current distribution were altered to target deep brain structures and structures in the mid-brain. The geometry and current distribution was altered to target specific fibers bundles, axonal tracts, or fibers of passage. The geometry and current distribution of the electrodes were altered to target cells with specific geometries.

One simulation configuration can be used and then another configuration followed by a delay in time.

To increase the focality of NCS several complimentary techniques are developed. These techniques may be used in combination, and which include:

Using multiple electrodes.
Controlling independently the current delivered to each electrode.
Controlling the current to target a specific brain region or structure.
Controlling the current to target a specific neurological disorder, cognitive function, or performance function.
Placing an apparatus to control or divide current or voltage between a stimulation source and the electrodes.
Changing the current delivered to each electrode over time.
Changing the current based on subject behavior.
Using three electrodes.
Applying a different current through each electrodes.
Applying a zero current through at least one electrode.
Targeting structures based on anatomical features.
Targeting structures to induce lasting changes in function.
Targeting the vasculature of the brain.
Altering geometry or material properties of an electrode or of any component associated with the electrode.
Using different gels/combination of gels at each plurality of electrodes
Using different metals at each plurality of electrodes
Using circular electrodes.
Using rectangular electrodes.
Enclosing at least a portion of the electrodes by at least one separate electrode.
Using concentric ring electrodes.
Using strip electrodes.
Using multiple electrodes having different shapes or material properties.
Using multiple concentric ring electrodes.
Adjusting geometry or material properties to induce lasting changes in function.
Altering geometry or material properties of any material placed between an electrode and the scalp.
Changing material or biological properties of the skin, skull, or hair.
Changing the number of electrodes.
Monitoring electrical properties of the electrodes and or patient before, during, or after stimulation.

A drug is administered in conjunction with electro-stimulation with the following results: the drug act in conjunction with the stimulation, the stimulation controls the release or targeting of the drug, or the stimulation and drug have different actions. In another embodiment, the drug stimulation accelerated the action of the drug. In another embodiment, the drug modulates the effects of the simulation. In yet another embodiment, the stimulation buffered the effects of the drug. In yet another embodiment, the drugs buffered the effects of stimulation.

In one example the metal is a mesh. In another example the metal is a solid plane. In yet another example the metal has a three dimensional surface.

In one example the electrodes have a shape of circle, triangle, rectangle, pentagon, hexagon, heptagon, octagon, ellipse, strip or annulus. In one embodiment all the electrode have the same shape. In another embodiment the electrodes have different shapes.

In one example, an extra-cephalic electrode is positioned on the body. In another example, an electrode of one plurality is portioned in an extra-cephalic location and electrodes of another plurality are positioned on the head.

In one example the head positioning cap can accommodate 1 to 500 electrodes. In another example, the head positioning cap can accommodate 3 to 200 electrodes. In yet another example, the head position cap can accommodate up to 700 electrodes.

In one example, and electrical controller is used. The electrical control includes an electrical circuit. The electrical controller may be controlled by a user or by an automatic system. In one embodiment, the electrical controller controls the current delivered to each electrode.

A focal-localized or functionalized—neurocranial electrostimulation system and method are taught. One embodiment of the method includes using multiple electrodes, with the current or voltage at each electrode controlled independently. Increasing focality refers to any controlled change or changes in the spatial distribution of the current, voltage, or function of the current or voltage, in any part(s) of the head or body.

According to another embodiment of the present invention, the shape, geometry, or material properties of the electrodes, or of materials attached or adjacent to the electrodes, are modified. Changing the geometry/shape of the electrodes refers to altering the configuration of the intrinsic shape of the NCS electrodes in terms of their relationships between lines, angles, and surfaces to give it a different form.

The electrode resistance may be suitably monitored before stimulation, during or after stimulation. In one embodiment the electrode resistance is monitored during stimulation. In another embodiment, the electrode resistance is monitored after stimulation. In a further embodiment, combined resistance of multiple electrodes is monitored. In a further embodiment, the parameters of stimulation are adjusted based on the electrode resistance.

One electrode of the first or second polarity is positioned in a way to stimulate a brain region selected from a group consisting of cortex, white matter, grey matter, cerebellum, cranial nerves, motor regions, prefrontal cortex, temporal lobe, sensory nerves, hippocampus, thalamus, basal ganglia. The positioning of the electrodes in a appropriate fashion would activate specific brain regions. In one embodiment, the center electrode in the 4×1 configuration is positioned over the target region. In another embodiment electrodes of a specific polarity are positioned near the target region.

In one embodiment, stimulation is applied during a memory task, a speaking task, a fluency task, as sleep task, a sleep/wake task, a recognition task, a selection task, a motor task, an attention task, a reasoning task, an attention task, a focus task, an understanding task, reaction time, a commercial task, a military task, a targeting task, general intelligence, a perception task, or a decision tasks.

In another embodiment stimulation is applied to an individual with symptoms associated with depression, movement disorder, Parkinson's disease, epilepsy, memory loss, stroke, obsessive compulsive disorder, sleep disorder, mood disorder, schizophrenia, manic disorder, attention deficit disorder, attention deficit hyper-activity, disorder, pain, chronic pain, tumor, carpal tunnel syndrome, coma, persistent vegetative state, Creutzfeldt-Jakob disease, narcolepsy, dyslexia, head injury, migraine, prion diseases, dementia, or neurological manifestations of AIDS.

In one example, stimulation is applied to induce a change in brain function including increasing excitability, decreasing excitability, change synaptic processing, changing neuronal firing rate, changing inhibitory function, changing excitatory function, decreasing synchronization, increasing synchronization, changing neuronal timing, triggering action potentials, inducing synaptic plasticity, changing brain oscillations, or changing sleep/wake related activity.

It will be appreciated that certain changes and modifications may be practiced within the scope of the appended claims. Accordingly, it should be recognized that other systems, functions, methods, and combinations thereof are possible in accordance with the present invention. Furthermore, although the invention is described with reference to specific embodiments and figures thereof, the embodiments and figures are merely illustrative, and not limiting of the scope of the invention.

We claim:

1. A method for electrostimulation comprising:
   providing a first electrode set comprising at least one electrode;
   providing a second electrode set comprising at least three electrodes, wherein the number of electrodes in the second electrode set is greater than the number of electrodes in the first electrode set;
   locating the first and the second sets of electrodes in a target area, the target area consisting of the exposed surface of the head and areas associated with the head of a subject;
   surrounding the first electrode set with the second electrode set, such that said electrodes of the second electrode set define a shape that surrounds the at least one electrode of the first electrode set; and
   delivering electric current from at least one electronic source to each of the electrodes in the first and second electrode sets, wherein all of the electrodes of the first electrode set are provided with a first electrical polarity opposite of a second electrical polarity provided to all of the electrodes of the second electrode set, and wherein no additional electrodes having a substantial current on the exposed surface of the head of said first polarity are provided outside said shape defined by said second electrode set, unless said additional electrodes are surrounded by electrodes having a substantial current of said second polarity, such that all electrodes provided on the exposed surface of the head and areas associated with the head of a subject having said first polarity and a substantial current are surrounded by electrodes having said second polarity, and
   wherein the total current delivered to the electrodes of the first electrode set is substantially equal in magnitude to the total current delivered to the electrodes of the second electrode set.

2. The method according to claim 1, wherein the second electrode set comprises at least three electrodes defining a shape selected from the group consisting of a circle, a triangle, a square and a polygon.

3. The method according to claim 1, wherein the number of electrodes in the second electrode set is selected from the group of 3 to 650 electrodes, 3 to 600 electrodes, 3 to 550 electrodes and 4 to 500 electrodes.

4. The method according to claim 2, wherein the first electrode set comprises one electrode and the electrodes of the second electrode set are spaced substantially equidistant from the one electrode of the first electrode set.

5. The method according to claim 1, wherein at least one electrode of the first or the second electrode sets has a shape selected from the groups consisting of circle, triangle, rectangle, pentagon, hexagon, heptagon, octagon, ellipse, strip, mesh, and annulus.

6. The method according to claim 1, wherein the electrodes of the first and the second electrode sets comprise of a material selected from the group consisting of silver, conducting rubber, platinum, copper, iron, steel and alloys thereof.

7. The method according to claim 1, further comprising monitoring electrode resistance.

8. The method according to claim 1, wherein at least one electrode of the first or second electrode set is suitably positioned to stimulate a brain region selected from a group consisting of cortex, white matter, grey matter, cerebellum, cranial nerves, motor regions, prefrontal cortex, temporal lobe, sensory nerves, hippocampus, thalamus, basal ganglia.

9. A method for electro stimulation comprising:
   providing a first electrode set comprising at least one electrode;
   providing a second electrode set comprising at least one annular electrode having an opening;
   locating the first and the second electrode sets in a target area, the target area consisting of the exposed surface of the head and areas associated with the head of a subject;
   placing at least one electrode of the first electrode set within the opening of the at least one annular electrode of the second electrode set; and
   delivering electric current from at least one electronic source respectively to the first and second electrode sets, wherein the first electrode set is provided with a first polarity, said first polarity of the first electrode set being opposite of a second polarity provided to the second electrode set, and wherein no additional electrodes having a substantial current on the exposed surface of the head of said first polarity are provided outside said electrodes of said second electrode set, unless said additional electrodes are surrounded by electrodes having a substantial current of said second polarity, or are provided for surrounding electrodes having a substantial current of said second polarity, such that all electrodes provided on the exposed surface of the head and areas associated with the head of a subject having one of said first and second polarities are surrounded by electrodes having the opposite of said first and second polarities, or surround electrodes having the opposite of said first and second polarities, and
   wherein the total current delivered to the electrodes of the first electrode set is substantially equal in magnitude to the total current delivered to the electrodes of the second electrode set.

10. The method according to claim 9, wherein the number of electrodes in the first electrode set is selected from a group consisting of 2 to 750 electrodes, 3 to 650 electrodes and 4 to 550 electrodes.

11. The method according to claim 1, wherein the peak current delivered to at least one electrode is greater than 1 mA.

12. The method apparatus according to claim 1, wherein the second electrode set comprises at least four electrodes.

13. The method of claim 1 wherein the head and the areas associated with the head are selected from the group consisting of the cranium, scalp, face, neck, ears, eyes, forehead, cheek, chin, nose and mouth.

14. The method of claim 1, wherein the step of delivering current at least one of: treats a human being suffering from a brain related ailment, affects human cognitive performance, and modulates brain function.

15. The method according to claim 9, wherein at least one electrode of the first or the second electrode set has a shape selected from the group consisting of circle, triangle, rectangle, pentagon, hexagon, heptagon, octagon, ellipse, strip and annulus.

16. The method according to claim 9, wherein the opening of the annular electrode has a shape selected from the group consisting of circle, triangle, quadrilateral, square, pentagon, hexagon, heptagon, octagon and ellipse.

17. The method according to claim 9, wherein the second electrode set comprises at least one ring shape electrode having a circular opening.

18. The method according to claim 9, wherein the second electrode set comprises two ring shape electrodes.

19. The method according to claim 9, wherein a distance between at least one electrode of the first electrode set and at least one annular electrode of the second electrode set is suitably selected from a range comprising of 1 cm to 50 cm, 2 cm to 40 cm, 3 cm to 30 cm and 3 cm to 25 cm.

\* \* \* \* \*

UNITED STATES PATENT AND TRADEMARK OFFICE
CERTIFICATE OF CORRECTION

PATENT NO.        : 8,718,778 B2                                            Page 1 of 1
APPLICATION NO.   : 12/937950
DATED             : May 6, 2014
INVENTOR(S)       : Bikson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 421 days.

Signed and Sealed this
Twenty-ninth Day of September, 2015

Michelle K. Lee
*Director of the United States Patent and Trademark Office*